United States Patent
Levine et al.

(10) Patent No.: US 9,671,412 B2
(45) Date of Patent: Jun. 6, 2017

(54) BECLIN 1 PHOSPHORYLATION

(71) Applicant: Board of Regents, The University of Texas System, Austin, TX (US)

(72) Inventors: Beth C. Levine, Dallas, TX (US); Richard C. Wang, Dallas, TX (US); Yongjie Wei, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 85 days.

(21) Appl. No.: 14/667,372

(22) Filed: Mar. 24, 2015

(65) Prior Publication Data

US 2015/0198614 A1    Jul. 16, 2015

Related U.S. Application Data

(63) Continuation of application No. PCT/US2013/059560, filed on Sep. 12, 2013.

(60) Provisional application No. 61/704,613, filed on Sep. 24, 2012.

(51) Int. Cl.

| | | |
|---|---|---|
| C07K 1/00 | (2006.01) | |
| C07K 14/00 | (2006.01) | |
| C07K 14/435 | (2006.01) | |
| C07K 14/46 | (2006.01) | |
| C07K 14/47 | (2006.01) | |
| C07K 14/81 | (2006.01) | |
| C07K 14/82 | (2006.01) | |
| C07K 16/00 | (2006.01) | |
| C07K 16/18 | (2006.01) | |
| C07K 16/42 | (2006.01) | |
| G01N 33/68 | (2006.01) | |
| C07K 16/44 | (2006.01) | |
| G01N 33/574 | (2006.01) | |

(52) U.S. Cl.
CPC ..... *G01N 33/6872* (2013.01); *C07K 14/4702* (2013.01); *C07K 14/82* (2013.01); *C07K 16/18* (2013.01); *C07K 16/44* (2013.01); *G01N 33/57484* (2013.01); *G01N 2440/14* (2013.01); *G01N 2800/52* (2013.01)

(58) Field of Classification Search
None
See application file for complete search history.

(56) References Cited

U.S. PATENT DOCUMENTS

2003/0190689 A1* 10/2003 Crosby ............. G01N 33/5041
435/7.23

OTHER PUBLICATIONS

Wang et al. Akt-mediated regulation of autophagy and tumorigenesis through Beclin 1 phosphorylation (Science 338(6109):956-9, Epub Oct. 25, 2012).*
ThermoScientific, Safety Data Sheet, product code: PA535393, product name Phospho-Beclin1 pSer234 Antibody, Dec. 22, 2015.*
Brozzi et al. (Molecular Biology of the Cell 23: 4444-4455, published online Sep. 19, 2012).*
Foletti et al. (The Journal of Neuroscience 21 (15): 5473-5483, Aug. 1, 2001).*

\* cited by examiner

*Primary Examiner* — Alana Harris Dent
(74) *Attorney, Agent, or Firm* — Richard Aron Osman

(57) ABSTRACT

Antibodies specific for human Beclin 1 protein phosphorylated Ser234, Ser295, Tyr229, Tyr233 or Try352 are useful in diagnosing diseases such as cancer and impaired autophagy. The invention further relates to human Beclin 1 mutated at Ser234, Ser295, Tyr229, Tyr233 or Try352 with a phospho-silencing residue and uses thereof.

18 Claims, No Drawings

BECLIN 1 PHOSPHORYLATION

This application claims priority to U.S. 61/704,613, filed Sep. 24, 2012.

This invention was made with government support under Grant Numbers ROI CA84254-S1 and RO1 CA109618 awarded by the National Institutes of Health (NIH) and National Cancer Institute (NCI). The government has certain rights in the invention.

INTRODUCTION

We have discovered novel phosphorylation sites on Beclin 1 that are targets of oncogenic signaling, including the signaling molecules Akt and EGFR. When either of these molecules is activated, as commonly occurs in human tumors, Beclin 1 undergoes phosphorylation at one or more of these sites, which results in autophagy suppression.

We have shown that Akt-mediated phosphorylation of Beclin 1 Ser234 and Ser295 contributes to Akt-mediated tumorigenesis. We have also shown that EGFR-mediated phosphorylation of Beclin 1 Tyr 229, Tyr 233, and Try 352 contribute EGFR-mediated tumorigenesis, and to tumor progression of non-small cell lung carcinomas with activating mutations in EGFR and that human tumors with active EGFR mutations have phosphorylation of tyrosine 233 (detectable by western blot analysis).

The detection of Beclin 1 Ser234, Ser295, Tyr 229, Tyr 233, and/or Try 352 phosphorylation in human tumors reveals important information about the tumor, clinical prognosis, and/or predictors of the tumor response to chemotherapeutic agents. These include the baseline status of Akt or EGFR activation, baseline marker of autophagy suppression by Akt or EGFR, and assessments of whether such tumor characteristics predict clinical prognosis, response to Akt or EGFR inhibitor therapy, and/or response to other chemotherapies.

Our invention describes molecular events that explain how oncogenes such as Akt and oncogenic receptor tyrosine kinases such as EGFR can inactivate the autophagy pathway, and teaches that the detection of these events in tumor samples is useful clinically in determining which types of cancers are likely to respond to Akt or EGFR inhibitors and/or therapies that block these Beclin 1 inhibitory phosphorylation events. This invention solves the problem of knowing which tumors in patients have direct Akt/EGFR-mediated suppression of autophagy and which are more likely to benefit from Akt/EGFR inhibitor therapy.

The invention provides compositions and methods for diagnosing and treating diseases associated with pathogenic Akt/EGFR-mediated regulation of autophagy or tumorigenesis through Beclin 1 phosphorylation. The invention provides detection of Beclin 1 Ser234, Ser295, Tyr229, Tyr233 and/or Tyr352 phosphorylation in human tumors as a marker of Akt/EGFR activation, autophagy suppression by Akt/EGFR, predictor of clinical prognosis, and/or predictor of response to Akt/EGFR inhibitor chemotherapy or other chemotherapeutic regimens

SUMMARY OF THE INVENTION

The invention provides antibodies specific for Beclin 1 phosphorylated Ser234, Ser295, Tyr 229, Tyr 233 or Try 352, which has specific binding affinity for Ser234, Ser295, Tyr 229, Tyr 233 or Try 352 phosphorylated human Beclin 1 protein. The antibody may be polyclonal or monoclonal, or be or comprise fragments of either which retain specific binding affinity for the specifically phosphorylated human-Beclin 1.

The invention also provides pharmaceutical compositions comprising the subject antibodies, such as in unit dosages and/or in combination with other therapeutic agents, particularly anti-cancer agents, particularly agents that inhibit Akt- or EGFR-mediated tumorigenesis or progression. In one example, the invention provides compositions comprising a subject antibody (a) specific for Beclin 1 Ser234 or Ser295 phosphorylation and a different Akt inhibitor; or (b) specific for Beclin 1 Tyr229, Tyr233 or Tyr352 phosphorylation and a different EGFR inhibitor.

The invention provides methods of making and using the subject antibodies, including methods of characterizing a Beclin 1 protein of a human cancer cell, comprising: detecting in the protein Ser234, Ser295, Tyr 229, Tyr 233, and/or Try 352 phosphorylation with a subject antibody.

The invention provides methods of characterizing a Beclin 1 protein of a human cancer cell, comprising: detecting in the protein Ser234, Ser295, Tyr 229, Tyr 233 or Try 352 phosphorylation, particularly wherein the cancer cell is derived from a person, and the detecting step detects elevated Ser234, Ser295, Tyr 229, Tyr 233 or Try 352 phosphorylation as compared with a negative control cell.

In particular embodiments of this aspect:

the method further comprises detecting Ser234, Ser295, Tyr 229, Tyr 233 or Try 352 phosphorylation in a panel of Beclin 1 proteins from different human cancer cells, and correlating the Ser234, Ser295, Tyr 229, Tyr 233 or Try 352 phosphorylation to cancer prognosis or cancer therapy response, such as to Akt or EGFR inhibitors, to use, establish or validate Beclin 1 Ser234, Ser295, Tyr 229, Tyr 233 or Try 352 phosphorylation as a biomarker;

the method further comprises prescribing, initiating or continuing an Akt/EGFR inhibitor therapy for the person;

the detecting step comprises immunohistochemistry, immunostaining, immunofluorescence or western blot assay;

the cancer cell is of a tissue sample derived from the breast, pancreas, stomach, liver, secretory gland, bladder, lung, skin, prostate gland, ovary, cervix, uterus, brain, eye, connective tissue, bone, muscles or vasculature; and/or the cancer cell is of a tissue sample derived from a breast tumor, a lung carcinoma, a colon carcinoma, a cervical carcinoma, an adenocarcinoma, a melanoma, a leukemia, a lymphoma, a glioma, a neuroblastoma, a retinoblastoma or a sarcoma.

The invention also provides a human Beclin 1 protein wherein Ser234, Ser295, Tyr 229, Tyr 233 or Try 352 is substituted with a phospho-silencing residue, particularly wherein the phospho-silencing residue is alanine or glycine.

The invention also provides polynucleotides encoding the subject protein, including Beclin 1 proteins and antibodies. The polynucleotides may be operably linked to a heterologous transcription regulating sequence for expression, and may be incorporated into vectors, cells, etc.

The invention also provides methods of promoting autophagy in a cell, comprising contacting the cell with the subject Beclin 1 proteins, particularly wherein the contacting step is effected by expressing in the cell a polynucleotide encoding the protein.

The invention includes all combinations of the recited particular embodiments. Further embodiments and the full scope of applicability of the invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DESCRIPTION OF PARTICULAR
EMBODIMENTS OF THE INVENTION

The invention provides antibodies specific for human Beclin 1 protein phosphorylated at Ser234, Ser295, Tyr 229, Tyr 233, and/or Try 352. The invention further provides polynucleotides encoding same, expression vectors comprising them, and methods of diagnosing diseases or disorders associated with impaired autophagy including cancer, neurodegenerative diseases, and infectious diseases, including viral diseases. For example, we generated data indicating that herpes virus proteins that shut off autophagy do so by binding to Beclin 1 and promoting Akt/EGFR-dependent phosphorylation at Ser234, Ser295, Tyr 229, Tyr 233 or Try 352. In particular experiments we showed herpes simplex virus protein (ICP34.5) required for the virus to cause neurological disease, which we previously showed inhibits Beclin 1 and autophagy (Orvedahl A et al. 2007, Cell Host & Microbe) acts by recruiting Akt to Beclin 1, resulting in phosphorylation at Beclin 1 Ser234/Ser295. Our studies indicate Akt inhibitors can be useful therapy for treating herpes simplex virus infections, and in particular HSV encephalitis. The invention further provides human Beclin 1 mutated at position Ser234, Ser295, Tyr 229, Tyr 233 or Try 352 with a phospho-silencing residue, polynucleotides encoding same and uses thereof in treating diseases associated with pathogenic Akt or EGFR-mediated regulation of autophagy or tumorigenesis through Beclin 1 phosphorylation.

Antibodies

According to a first aspect, the invention provides an antibody specific for a phosphorylated human Beclin 1 protein, wherein the phosphorylation is at Ser234, Ser295, Tyr 229, Tyr 233 or Try 352. According to one embodiment the antibody is polyclonal. According to another embodiment the antibody is monoclonal.

The term "antibody" is used in the broadest sense and specifically covers antibodies (including full length monoclonal antibodies) and antibody fragments so long as they recognize human Beclin 1 which is phosphorylated at position Ser234, Ser295, Tyr 229, Tyr 233 or Try 352. An antibody molecule is usually monospecific, but may also be described as idiospecific, heterospecific, or polyspecific. Antibody molecules bind by means of specific binding sites to specific antigenic determinants or epitopes on antigens. "Antibody fragments" comprise a portion of a full length antibody, generally the antigen binding or variable region thereof. Examples of antibody fragments include Fab, Fab', F(ab').sub.2, and Fv fragments; diabodies; linear antibodies; single-chain antibody molecules; and multispecific antibodies formed from antibody fragments.

Monoclonal antibodies (MAbs) may be obtained by methods known to those skilled in the art. See, for example Kohler et al (1975); U.S. Pat. No. 4,376,110; Ausubel et al (1987-1999); Harlow et al (1988); and Colligan et al (1993), the contents of which references are incorporated entirely herein by reference. The mAbs of the invention may be of any immunoglobulin class including IgG, IgM, IgE, IgA, and any subclass thereof. A hybridoma producing an mAb may be cultivated in vitro or in vivo. High titers of mAbs can be obtained in in vivo production where cells from the individual hybridomas are injected intraperitoneally into mice, such as pristine-primed Balb/c mice to produce ascites fluid containing high concentrations of the desired mAbs. MAbs of isotype IgM or IgG may be purified from such ascites fluids, or from culture supernatants, using column chromatography methods well known to those of skill in the art.

Besides the conventional method of raising antibodies in vivo, antibodies can be generated in vitro using phage display technology. Such a production of recombinant antibodies is much faster compared to conventional antibody production and they can be generated against an enormous number of antigens. In contrast, in the conventional method, many antigens prove to be non-immunogenic or extremely toxic, and therefore cannot be used to generate antibodies in animals. Moreover, affinity maturation (i.e., increasing the affinity and specificity) of recombinant antibodies is very simple and relatively fast. Finally, large numbers of different antibodies against a specific antigen can be generated in one selection procedure. To generate recombinant monoclonal antibodies one can use various methods all based on phage display libraries to generate a large pool of antibodies with different antigen recognition sites. Such a library can be made in several ways: One can generate a synthetic repertoire by cloning synthetic CDR3 regions in a pool of heavy chain germline genes and thus generating a large antibody repertoire, from which recombinant antibody fragments with various specificities can be selected. One can use the lymphocyte pool of humans as starting material for the construction of an antibody library.

The invention provides kits for analyzing the level of Beclin 1 that is phosphorylated at position Ser234, Ser295, Tyr 229, Tyr 233 or Try 352 in a biological test sample; the kit comprises the antibody of the invention. In one embodiment, the kit is identified for diagnosing cancer. In another embodiment the kit is identified for diagnosing degenerative diseases. In some embodiments, the kit contains, in addition to the antibody according to the invention, additional reagents such as buffers, solutions for sample preparation, solutions for detecting the reagent, including instructions for use for carrying out the test.

Diagnostics

The invention provides methods for diagnosing a disease associated with pathogenic Akt/EGFR-mediated regulation of autophagy or tumorigenesis through Beclin 1 Ser234, Ser295, Tyr 229, Tyr 233 or Try 352 phosphorylation, including cancers, neurodegenerative diseases, and infectious diseases comprising detecting the presence of Beclin 1 phosphorylation at Ser234, Ser295, Tyr 229, Tyr 233 or Try 352 Ser295 in a biological test sample, particularly using a subject antibody or antigen binding fragments thereof, wherein an elevated amount of Beclin 1 phosphorylation at position Ser234, Ser295, Tyr 229, Tyr 233 or Try 352 in the sample relative to the amount of the same Beclin 1 phosphorylation in a standard or control sample is indicative of disease.

The invention provides a method for diagnosing a disease associated with pathogenic Akt/EGFR-mediated regulation of autophagy or tumorigenesis through Beclin 1 Ser234, Ser295, Tyr 229, Tyr 233 or Try 352 phosphorylation, particularly a cancer, neurodegenerative disease or infection, comprising: (a) obtaining a biological test sample; (b) contacting the test sample with a subject antibody (including an antigen-binding fragment thereof), under conditions such that a complex can form between the phosphorylated Beclin 1 and the antibody, and quantifying the amount of the complex, thereby quantifying the amount of phosphorylated Beclin 1 in the biological test sample; and (c) comparing the amount of phosphorylated Beclin 1 in the biological test sample to a standard or control sample; wherein an elevated amount of phosphorylated Beclin 1 in said biological test sample relative to the standard or control sample is indicative of the disease.

According to one embodiment an increase in the amount of Beclin 1 phosphorylated at Ser234, Ser295, Tyr 229, Tyr 233 or Try 352 in a biological test sample relative to a standard or control sample, is indicative of disease, or disease type or staging, e.g. candidacy for Akt/EGFR inhibitor therapy. According to some embodiments the amount of Beclin 1 phosphorylated at position Ser234, Ser295, Tyr 229, Tyr 233 or Try 352 is increased by at least 10%, 25%, 50%, 75%, 90% or 95% relative to a standard or control sample. According to another embodiment the presence of Beclin 1 phosphorylated at position Ser234, Ser295, Tyr 229, Tyr 233 or Try 352 in a biological test sample is indicative of cancer in said biological test sample. The standard or control sample may be taken from a healthy subject or from a healthy tissue of a subject.

The methods can be used to indicate the suitability of a variety of Akt/EGFR inhibitors, including inhibitors that compete for the ATP/EGFR-binding site, e.g. that prevent the generation of PIP3 by PI-3 K or block binding of PIP3 to Akt (e.g. phosphatidylinositol analogs, TCL1-derived peptide), prevent activation of Akt/EGFR via inhibition of upstream affectors (e.g. Akt Inhibitor IV, Akt Inhibitor V, Triciribine.

According to some embodiments the biological test sample is a tissue sample, which may be derived from the breast, pancreas, stomach, liver, secretory gland, bladder, lung, skin, prostate gland, ovary, cervix, uterus, brain, eye, connective tissue, bone, muscles or vasculature. According to other embodiments the biological test sample is a tumor sample, or an isolate thereof, which may be directly or indirectly derived from a human subject, and which may be a breast tumor, a lung carcinoma, a colon carcinoma, a cervical carcinoma, an adenocarcinoma, a melanoma, a leukemia, a lymphoma, a glioma, a neuroblastoma, a retinoblastoma, and a sarcoma. The term "tumor" as used herein includes both primary tumors, which may be benign or malignant, as well as secondary tumors, and metastases, which have spread to other sites in the body. The tumor may be a solid tumor or a non-solid tumor. According to other embodiments the biological test sample is a biological fluid or an isolate thereof, which may be blood, serum or lymph.

According to certain embodiments, the tumor sample or biological fluid may comprise a tumor cell having increased amounts of Ser234, Ser295, Tyr 229, Tyr 233 or Try 352 phosphorylated Beclin 1 protein relative to the amounts of Ser234, Ser295, Tyr 229, Tyr 233 or Try 352 phosphorylated Beclin 1 in cells of healthy subjects or normal cells, such as surrounding the tumor.

The subject neurodegenerative diseases include for example Alzheimer's disease, Huntington's disease, Parkinson's disease, neurodegeneration due to stroke, amyotrophic lateral sclerosis, Pick's disease, Progressive Supranuclear Palsy (PSP), fronto-temporal dementia (FTD), pallidoponto-nigral degeneration (PPND), Guam-ALS syndrome, pallido-nigro-luysian degeneration (PNLD) and corticobasal degeneration (CBD).

In particular embodiments the amount of phosphorylated Beclin 1 is determined by a method such as radioimmunoassay, immunohistochemistry, immunostaining, immunofluorescence assays, and western blot analysis.

Immunohistochemistry as used herein refers to a method which involves detection of a substrate in situ in fixed cells by substrate specific antibodies according to embodiments of the invention. The substrate specific antibodies may be linked to fluorophores (as in the case of immunofluorescence). Detection is by microscopy and subjective or automatic evaluation. It will be appreciated that immunohistochemistry is often followed by counterstaining of the cell nuclei using for example Hematoxylin or Giemsa stain.

Immunoassays may be carried out in liquid or on biological support. For instance, a sample (e.g., blood, plasma, stool, urine, cells, tissue, cerebral spinal fluid, body fluids, etc.) can be brought in contact with a solid phase support or carrier (such as nitrocellulose or plastic) that comprises an antibody of the invention capable of specifically recognizing human Beclin 1 phosphorylated at position Ser234, Ser295, Tyr 229, Tyr 233 or Try 352. The support may then be contacted with a second antibody, which recognizes preferably a second site different from the site recognized and bound by the antibody of the invention or antigen binding fragments thereof. The second antibody can be detectably labeled, e.g., with a fluorescent label or an enzyme, or it can be labeled by a secondary labeling reagent that binds to it specifically, and then its presence measured by conventional means for detecting the label.

A "solid phase support or carrier" includes any support capable of binding an antigen, antibody, or other specific binding partner. Supports or carriers include glass, polystyrene, polypropylene, polyethylene, dextran, nylon, amylases, natural and modified celluloses, and polyacrylamides. A support material can have any structural or physical configuration. Thus, the support configuration may be spherical, as in a bead, or cylindrical, as in the inside surface of a test tube, or the external surface of a rod. Alternatively, the surface may be flat such as a sheet, test strip, etc.

Beclin 1 Variants

The invention provides a human Beclin 1 variant, wherein one or more of Ser234, Ser295, Tyr 229, Tyr 233 or Try 352 is/are substituted with a phospho-silencing residue, which is incapable of phosphorylation. According to one embodiment the phospho-silencing residue is alanine or glycine.

The invention provides a recombinant polynucleotide construct wherein a polynucleotide encoding a human Beclin 1 variant of the invention, is operably linked to transcription regulating sequences that will direct the transcription of the polynucleotide in the intended host cell. In another embodiment, the transcription regulating sequences are transcription initiation regulating sequences. The invention further provides a vector comprising a recombinant polynucleotide construct encoding a human Beclin 1 variant of the invention. According to various embodiments the vector is for example, a plasmid or a virus. The recombinant polynucleotide construct may be expressed in a host cell selected from eukaryotic and prokaryotic.

The invention provides an isolated polynucleotide encoding a human Beclin 1 variant, wherein Ser234, Ser295, Tyr 229, Tyr 233 or Try 352 of the human Beclin 1 variant is substituted with a phospho-silencing residue.

An "isolated polynucleotide" refers to a polynucleotide segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to polynucleotides, which have been substantially purified from other components, which naturally accompany the polynucleotide in the cell, e.g., RNA or DNA or proteins. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA, which is part of a hybrid gene encoding additional polypeptide sequence, and RNA such as mRNA.

A "construct" means any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more polynucleotide molecule has been linked in a functionally operative manner, i.e. operably linked. A recombinant construct will typically comprise the polynucleotides of the invention operably linked to transcriptional initiation regulatory sequences that will direct the transcription of the polynucleotide in the intended host cell. Both heterologous and non-heterologous (i.e., endogenous) promoters can be employed to direct expression of the nucleic acids of the invention.

A "vector" refers any recombinant polynucleotide construct that may be used for the purpose of transformation, i.e. the introduction of heterologous DNA into a host cell. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors".

An "expression vector" as used herein refers to a nucleic acid molecule capable of replication and expressing a gene of interest when transformed, transfected or transduced into a host cell. The expression vectors comprise one or more phenotypic selectable markers and an origin of replication to ensure maintenance of the vector and to, if desired, provide amplification within the host. The expression vector further comprises a promoter to drive the expression of the polypeptide within the cells. Suitable expression vectors may be plasmids derived, for example, from pBR322 or various pUC plasmids, which are commercially available. Other expression vectors may be derived from bacteriophage, phagemid, or cosmid expression vectors.

Methods for manipulating a vector comprising an isolated polynucleotide are well known in the art and include direct cloning, site-specific recombination using recombinases, homologous recombination, and other suitable methods of constructing a recombinant vector. The expression vector comprising the polynucleotide of interest is introduced into the cells by any means appropriate for the transfer of DNA into cells. Many such methods are well known in the art.

The invention provides a recombinant polynucleotide construct wherein a polynucleotide encoding any of the human Beclin 1 variants of the invention, is operably linked to a transcription regulating sequences that will direct the transcription of the polynucleotide in the intended host cell. In another embodiment, the transcriptional regulating sequences are transcriptional initiation regulating sequences. The invention further provides vectors comprising the recombinant polynucleotide constructs encoding the human Beclin 1 variants of the invention, the vector being a plasmid or a virus. Consequently, the recombinant polynucleotide construct may be expressed in a host cell selected from eukaryotic and prokaryotic.

Therapies

The constructs, vectors and compositions of the invention are useful for the treatment of cancer, neurodegenerative and infectious, particularly viral, diseases and other conditions in which inappropriate or detrimental expression of the human Beclin 1 and/or human Akt/EGFR gene is a component of the etiology or pathology of the condition, as detailed herein below.

The invention provides a method for treating cancer or inhibiting tumor progression in a subject in need thereof comprising expressing in cells of the subject a human Beclin 1 variant having a phospho-silencing residue at position of Ser234, Ser295, Tyr 229, Tyr 233 or Try 352. According to some embodiments the expression of the human Beclin 1 variant having a phospho-silencing residue at position of Ser234, Ser295, Tyr 229, Tyr 233 or Try 352 in cells of the subject induces autophagy, induces cell death, or restores cell growth control, thereby treating cancer or inhibiting tumor progression in the subject.

According to another embodiment, the method for treating cancer or inhibiting tumor progression comprises the administration to a subject of a therapeutically effective amount of a recombinant polynucleotide construct comprising a polynucleotide encoding a subject human Beclin 1 variant. The construct may be introduced into the subject's cells ex vivo or in situ.

According to another embodiment, the subject to be treated by methods and compositions of the invention has a tumor characterized by elevated expression or activity of Akt/EGFR in at least a portion of the cells of the tumor as compared to the expression or activity of Akt/EGFR in healthy cells or tissues According to another embodiment, the invention provides a method of selectively inducing, enhancing or promoting autophagy in target cells, comprising expressing in target cells a polynucleotide encoding a subject human Beclin 1 variant. According to some embodiments the target cells are cells in which the expression or activity of Akt/EGFR is present or significantly increased.

The invention further provides the use of the recombinant polynucleotide construct according to some embodiments of the invention for the manufacture of a medicament for treating cancer or inhibiting tumor progression in a subject.

In certain embodiments, the polynucleotide constructs of the invention can be used to treat cancer alone or in combination with other established or experimental therapeutic regimens against cancer. Therapeutic methods for treatment of cancer suitable for combination with the invention include, but are not limited to, chemotherapy, radiotherapy, phototherapy and photodynamic therapy, surgery, nutritional therapy, ablative therapy, combined radiotherapy and chemotherapy, brachitherapy, proton beam therapy, immunotherapy, cellular therapy, and photon beam radiosurgical therapy.

The invention further provides a method of screening for a molecule that influences the intracellular concentration of human Beclin 1 phosphorylated at Ser234, Ser295, Tyr 229, Tyr 233 or Try 352, comprising: (a) adding a putative molecule to a cell expressing human Beclin 1; (b) contacting the cell with an antibody of the invention or antigen binding fragment thereof, under conditions such that a complex can form between phosphorylated Beclin 1 and the antibody and quantifying the amount of the complex, thereby quantifying the amount of phosphorylated Beclin 1 in the biological test sample; and (c) comparing the amount of phosphorylated Beclin 1 in the cell in the presence and absence of said putative molecule. According to one embodiment, the putative molecule decreases the intracellular concentration of the Ser234, Ser295, Tyr 229, Tyr 233 or Try 352 phosphorylated human Beclin 1.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

EXAMPLES

1. Akt-Mediated Regulation of Autophagy and Tumorigenesis Through Beclin 1 Phosphorylation Aberrant signaling through the class I phosphatidylinositol 3-kinase (PI3K)-Akt axis is frequent in human cancer. Here we show that Beclin 1, an essential autophagy and tumor suppressor protein, is a target of the protein kinase Akt. Expression of a Beclin 1 mutant resistant to Akt-mediated phosphorylation increased autophagy, reduced anchorage-independent growth, and inhibited Akt-driven tumorigenesis. Akt-mediated phosphorylation of Beclin 1 enhanced its interactions with 14-3-3 and vimentin intermediate filament proteins, and vimentin depletion increased autophagy and inhibited Akt-driven transformation. Thus, Akt-mediated phosphorylation of Beclin 1 functions in autophagy inhibition, oncogenesis, and the formation of an autophagy-inhibitory Beclin-1/14-3-3/vimentin intermediate filament complex. These findings have broad implications for targeting Akt signaling and intermediate filament proteins in autophagy and cancer.

Mutations leading to activation of the serine/threonine kinase Akt are frequent in human cancer (1). Akt has many downstream targets involved in tumorigenesis, including mTOR (mammalian target of rapamycin) (2). Akt also inhibits autophagy (3), a lysosomal degradation pathway that removes unwanted or damaged cellular constituents and functions in tumor suppression (4). Akt suppression of autophagy can be mediated by activation of mTOR, which inhibits the autophagy-initiating ULK1 kinase complex (4).

We investigated whether Akt inhibits autophagy by directly regulating the core autophagy machinery independently of mTOR. Expression of constitutively active myristoylated (5) and tagged Akt1 (Flag-tagged myr-Akt) in HeLa cells inhibited autophagy during growth in normal medium, in response to serum and amino acid starvation (a physiological inducer of autophagy), in response to treatment with an ATP-competitive inhibitor of mTOR, Torin1 (6), and in response to both starvation and Torin1 treatment. In all conditions, cells expressing myr-Akt1 had decreased numbers of puncta upon transfection with a fusion protein of green fluorescent protein with LC3 (GFP-LC3), a fluorescent marker of autophagosomes; increased amounts of p62 (a substrate that is degraded by autophagy); and increased amounts of the cytosolic non-lipidated form of LC3, LC3-I, and of total LC3 (7). Amounts of phospho-4E-BP1, a phosphorylation target of mTOR, were decreased in Torin1-treated cells, including those expressing myr-Akt1. Thus, myr-Akt1 suppresses basal autophagy, starvation-induced autophagy, and Torin1-induced autophagy, indicating that active Akt can inhibit autophagy through mTOR-independent mechanisms.

We examined whether autophagy execution proteins could be targets of Akt. We focused on Beclin 1 because of its role in autophagy and tumor suppression (4). Endogenous Akt co-immunoprecipitated with endogenous Beclin 1 in HeLa cells, and this interaction was weakened by starvation. In contrast, the interaction of myr-Akt1 with a Flag epitope-tagged construct of Beclin 1 was not affected by starvation. Kinase prediction algorithms (8, 9) showed Beclin 1 to contain a motif that resembles the consensus Akt phosphoryation motif (10) and another sequence that corresponds to a 14-3-3 protein binding motif (which can be generated by Akt phosphorylation). Phosphospecific antibodies against these two candidate phosphorylation sites in Beclin 1 ($S^{234}$ and $S^{295}$) recognized wild-type Flag-Beclin 1 expressed in HeLa cells and immunoreactivity was decreased with the corresponding Flag-Beclin 1 alanine substitution mutant. GST-Akt1 phosphorylated Beclin 1 $S^{295}$ but not Beclin 1 $S^{234}$ in vitro, and this was partially blocked by treatment with two Akt inhibitors, MK-2206 and Akt inhibitor X. Expression of active Akt1 (myr-Akt1) increased and expression of a catalytically inactive, non-phosphorylatable Akt1 mutant (K179M/T308A/S473A; DN-Akt1) decreased, respectively, phosphorylation of Flag-Beclin 1 $S^{295}$ and Flag-Beclin 1 $S^{234}$ in HeLa cells. Expression of myr-Akt1 also led to phosphorylation of endogenous Beclin 1 $S^{295}$ and endogenous Beclin 1 $S^{234}$ which was not reversed by mTOR inactivation with Torin1. Endogenous Beclin 1 $S^{295}$ phosphorylation increased when starved HeLa cells were fed with normal medium. Together, these studies demonstrate that Beclin 1 is phosphorylated by Akt on residue 295 (and 234) in an mTOR-independent manner.

We compared the phosphorylation of Beclin 1 $S^{295}$ in three paired sets of tumor cell lines with and without Akt activation. Melanoma cells with mutant PTEN (WM793) had more phosphorylation of Beclin 1 $S^{295}$ than did those with wild-type PTEN (451Lu) (11). U87-MG glioblastoma cells with high Akt activity due to inactivating mutations in PTEN showed more phosphorylation of Beclin 1 $S^{295}$ than did U87-MG cells in which wild-type PTEN was reintroduced (12). In breast carcinoma cells, $S^{295}$ phosphorylation was detected in MCF10A-DCIS cells with an activating H1047R mutation in PIK3CA but not in MDA-MB231 cells lacking constitutive Akt activation (13). Thus, in three different tumor types, activation of Akt is associated with phosphorylation of Beclin 1 $S^{295}$, indicating that phosphorylation of Beclin 1 $S^{295}$ is common in human tumors with activated Akt.

We transfected MCF7 human breast carcinoma cells [which express low amounts of endogenous Beclin 1 (14)] with GFP-LC3 and wild-type Beclin 1 or Beclin 1 S295A or AA mutants. Cells transfected with S295A and AA mutants had increased basal (but not starvation-induced) autophagy Inhibition of Akt by MK-2206 increased basal autophagy in MCF7 cells to a lesser extent in cells transfected with Beclin 1 AA than in cells transfected with wild-type Beclin 1. Conversely, expression of active Akt decreased basal autophagy in all MCF7 cells, but cells expressing Beclin 1 AA showed more autophagy than cells expressing wild-type Beclin 1 or vector alone. Thus, Akt inhibits basal autophagy both through Beclin 1 phosphorylation-dependent and independent mechanisms.

To examine the role of Akt-mediated Beclin 1 phosphorylation in Akt-driven tumorigenesis, we transduced Rat2 fibroblasts with myr-Akt1 (which transforms rat fibroblasts (15)) and either wild-type Beclin 1 or Beclin 1 phosphorylation site mutants. Myr-Akt1 suppressed autophagy in Rat2 fibroblasts, reduced co-immunoprecipitation of Class III PI3K Vps34 with Beclin 1, and decreased Beclin 1-associated lipid kinase activity. The autophagy suppressive effects of active Akt were largely prevented by expression of the Beclin 1 AA mutant and mildly decreased by the Beclin 1 S295A mutant. Expression of myr-Akt1 had minimal effects on the interaction of Beclin 1 AA and Vps34 or on the amounts of Beclin 1 AA-associated Vps34 activity. Thus, myr-Akt1 suppresses Beclin 1-associated Vps34 activity and autophagy in a manner that is partially reversed by a Beclin 1 mutant resistant to Akt-mediated phosphorylation.

In an anchorage-independence growth assay, shRNA depletion of Beclin 1 or myr-Akt1 expression caused Rat2 fibroblasts to form numerous colonies in soft agar. Both the number and size of colonies formed by myr-Akt1-expressing cells were significantly reduced by co-expression of Beclin 1 AA. Rat2 cells expressing myr-Akt1 also had higher amounts of endogenous Beclin 1 $S^{295}$ phosphorylation than control cells. Thus, active Akt1 promotes Beclin 1 $S^{295}$ phosphorylation, and expression of a non-phosphorylatable mutant of Beclin 1 suppresses Akt-mediated transformation in vitro. Inactivation of Beclin 1 by Akt-mediated phosphorylation can therefore contribute to Akt's transforming properties.

Beclin 1 AA also suppressed myr-Akt1-driven tumorigenesis in vivo. All myr-Akt1-expressing Rat2 cells formed tumors in immunodeficient NOD SCID® mice, but tumor growth rate and tumor mass upon necropsy were less for cells expressing Beclin 1 AA than for cells expressing wild-type Beclin 1 or myr-Akt1 alone. Tumors expressing myr-Akt1 alone had numerous cells displaying p62 immunoreactivity (indicating autophagy suppression) whereas very few p62 immunoreactive cells were detected in tumors from cells expressing both myr-Akt1 and Beclin 1 AA. Tumors expressing myr-Akt1 alone or active Akt and Beclin 1 resembled fibrosarcomas; 94% (17/18) showed tissue invasion and 50% (9/18) exhibited nuclear pleomorphism and decreased nucleus:cytoplasmic ratios. Tumors expressing myr-Akt1 and Beclin 1 AA formed less cellular, more disorganized tumors with limited or no tissue invasion; 60% (6/10) displayed degenerative features with numerous pyknotic nuclei. Tumors expressing active Akt alone or with Beclin 1 had higher mean mitotic counts (n=8.39; n=8.37, respectively) than tumors expressing myr-Akt1 and Beclin 1 AA (n=3.67) ($P<0.0001$). They also had increased Ki-67 labeling, and decreased TUNEL staining. Thus, the expression of a mutant of Beclin 1 that cannot be phosphorylated by Akt increases tumor cell autophagy, decreases tumor growth rate and size, decreases tumor cellular proliferation, and increases tumor cell death. These results indicate a role for Akt-mediated Beclin 1 phosphorylation in the tumorigenic effects of Akt.

To investigate how Akt phosphorylation of Beclin 1 inhibits autophagy, we determined whether Akt-mediated phosphorylation of Beclin 1 generates a 14-3-3 binding motif (10). Endogenous 14-3-3 proteins and Beclin 1 co-immunoprecipitated in HeLa cells and this interaction decreased during starvation. Mutation of predicted Beclin 1 14-3-3 binding sites, S234A or S295A, weakened the Beclin 1/14-3-3 interaction and the double mutation (AA) nearly completely abolished Beclin 1/14-3-3 binding. Similar amounts of Atg14, a component of the autophagy-inducing Beclin 1/Class III PI3K complex (16), immunoprecipitated with WT and non-phosphorylatable mutants of Beclin 1, indicating these mutations do not cause major alterations in protein stability or folding. Expression of myr-Akt1 blocked starvation-induced disruption of 14-3-3/Beclin 1 binding and conversely, expression of DN-Akt1 inhibited 14-3-3/Beclin 1 binding during growth in normal medium. Thus, Beclin 1 interacts with 14-3-3 proteins through S234 and S295, and this interaction is negatively regulated by starvation and Akt inhibition.

14-3-3 proteins can regulate their binding partners' functions through interactions with intermediate filaments (17, 18). The intermediate filaments, keratin 18 (K18) and vimentin, immunoprecipitated with Flag-Beclin 1 in HeLa cells and this was reduced by expression of DN-Akt1. Immunoprecipitation of Flag-Beclin 1 was increased by mutants of vimentin and K18 with increased binding to 14-3-3 proteins (K18 R89C (19)) but decreased with mutants with decreased binding to 14-3-3 proteins (K18S33A (19) and vimentin S39A). The Flag-Beclin 1 AA mutant did not immunoprecipitate with wild-type vimentin-GFP. siRNA targeted against 14-3-3ε abolished the interaction between Flag-Beclin 1 and vimentin-GFP. Thus, Beclin 1 interacts with 14-3-3 proteins and intermediate filament proteins through a mechanism involving the $S^{234}$ and $S^{295}$ Akt phosphorylation/14-3-3 binding sites of Beclin 1 and the 14-3-3 binding sites of intermediate filament proteins.

In Rat2 cells, expression of myr-Akt1 increased the interactions of endogenous 14-3-3 proteins and vimentin (the major intermediate filament protein expressed in fibroblasts (20)) with endogenous Beclin 1 in parallel with its increased phosphorylation. Expression of active Akt had little effect on the binding of Beclin 1 AA with 14-3-3 proteins and vimentin. Thus, active Akt can promote the interaction of Beclin 1 with vimentin through phosphorylation of Beclin 1 and generation of 14-3-3 binding sites.

Wild-type Beclin 1 had a diffuse cytoplasmic localization in the absence of active Akt expression, and localization of Beclin 1 with vimentin was observed primarily in a perinuclear pattern. Expression of myr-Akt1 redistributed wild-type Beclin 1 into a reticular pattern and increased Beclin 1/vimentin colocalization, but did not have these effects on Beclin 1 AA. Conversely, starvation decreased Beclin 1/vimentin colocalization in a reticular pattern. Thus, active Akt enhances the colocalization of Beclin 1 with vimentin in Rat2 cells in a manner that requires the Beclin 1 Akt phosphorylation and 14-3-3 binding sites $S^{234}$ and $S^{295}$.

In Rat2 cells, two different shRNAs that target vimentin increased autophagy. Vimentin appears to inhibit autophagy downstream of Beclin 1 phosphorylation because depletion of vimentin also increased autophagy in Rat2 fibroblasts expressing myr-Akt1. This increased autophagy was associated with inhibition of Akt-mediated transformation; vimentin shRNAs significantly inhibited the number and size of Rat2 colonies formed in soft agar. Thus, the regulation of Beclin 1/vimentin interactions by active Akt provides a mechanism for both inhibition of autophagy by intermediate filaments and for Akt-mediated transformation. As in the case of the interaction of AMBRA1 with the dynein motor complex (21), these data indicate that interactions between core autophagy proteins and cytoskeletal elements can regulate autophagy.

In this work we performed subtractive IP: mass spectroscopy experiments to identify proteins that bind to Beclin 1 when it is phosphorylated but not when it is not phosphorylated. The major protein we found was keratin 10. Although keratins are often contaminants in these types of experiments, we confirmed the interaction was real, and worked backwards to deduce that keratins bind to 14-3-3 molecules that bind to phosphorylation sites generated by Akt—thereby developing our working hypothesis that Akt could promote the phosphorylation of these sites on Beclin 1. Larance et al. (22) used a computer-based bioinformatics analysis of novel insulin-responsive proteins, including murine Beclin 1 to computer-predict potential 14-3-3 sites, and supplementary Table 2 predicts potential phosphorylation sites in homologous murine residues; however no actual phosphorylation was shown or suggested, in either normal or cancer cells. Our hypothesis that Akt-mediated phosphorylation of Beclin 1 is important for autophagy suppression and Akt-driven tumorigenesis derived from our experimental results (supra), and could not have derived from a computer prediction of potential Akt phosphorylation sites on Beclin 1. Our findings demonstrate a link between oncogenic signaling, the core autophagy machinery, and cytoskeletal proteins in the intermediate filament family. Akt signaling, intermediate filaments and 14-3-3 proteins are mechanistically linked to autophagy inhibition and tumorigenesis through regulation of the Beclin 1 complex. Our findings also demonstrate a specific mechanism by which autophagy can be suppressed in human cancer.

REFERENCES

1. D. A. Altomare, J. R. Testa, Perturbations of the AKT signaling pathway in human cancer. *Oncogene* 24, 7455 (2005).
2. J. A. Engelman, J. Luo, L. C. Cantley, The evolution of phosphatidylinositol 3-kinases as regulators of growth and metabolism. *Nat Rev Genet* 7, 606 (2006).
3. M. Degtyarev et al., Akt inhibition promotes autophagy and sensitizes PTEN-null tumors to lysosomotropic agents. *J Cell Biol* 183, 101 (2008).
4. B. Levine, G. Kroemer, Autophagy in the pathogenesis of disease. *Cell* 132, 27 (2008).
5. J. S. Boehm et al., Integrative genomic approaches identify IKBKE as a breast cancer oncogene. *Cell* 129, 1065 (2007).
6. C. C. Thoreen et al., An ATP-competitive mammalian target of rapamycin inhibitor reveals rapamycin-resistant functions of mTORC1. *J Biol Chem* 284, 8023 (2009).
7. N. Mizushima, T. Yoshimori, B. Levine, Methods in mammalian autophagy research. *Cell* 140, 313 (2010).
8. J. C. Obenauer, L. C. Cantley, M. B. Yaffe, Scansite 2.0: Proteome-wide prediction of cell signaling interactions using short sequence motifs. *Nucleic Acids Res* 31, 3635 (2003).
9. Y. Xue et al., GPS 2.0, a tool to predict kinase-specific phosphorylation sites in hierarchy. *Mol Cell Proteomics* 7, 1598 (2008).
10. B. D. Manning, L. C. Cantley, AKT/PKB signaling: navigating downstream. *Cell* 129, 1261 (2007).
11. K. H. Paraiso et al., PTEN loss confers BRAF inhibitor resistance to melanoma cells through the suppression of BIM expression. *Cancer Res* 71, 2750 (2011).
12. M. Y. Wang et al., Mammalian target of rapamycin inhibition promotes response to epidermal growth factor receptor kinase inhibitors in PTEN-deficient and PTEN-intact glioblastoma cells. *Cancer Res* 66, 7864 (2006).
13. N. Y. Kalaany, D. M. Sabatini, Tumours with PI3K activation are resistant to dietary restriction. *Nature* 458, 725 (2009).
14. X. H. Liang et al., Induction of autophagy and inhibition of tumorigenesis by *beclin* 1. *Nature* 402, 672 (1999).
15. J. D. Carpten et al., A transforming mutation in the pleckstrin homology domain of AKT1 in cancer. *Nature* 448, 439 (2007).
16. C. He, B. Levine, The Beclin 1 interactome. *Current Opin Cell Biol* 22, 140 (2010).
17. S. S. Margolis et al., Role for the PP2A/B56delta phosphatase in regulating 14-3-3 release from Cdc25 to control mitosis. *Cell* 127, 759 (2006).
18. S. Kim, P. Wong, P. A. Coulombe, A keratin cytoskeletal protein regulates protein synthesis and epithelial cell growth. *Nature* 441, 362 (2006).
19. N. O. Ku, J. Liao, M. B. Omary, Phosphorylation of human keratin 18 serine 33 regulates binding to 14-3-3 proteins. *EMBO J* 17, 1892 (1998).
20. W. W. Franke, E. Schmid, S. Winter, M. Osborn, K. Weber, Widespread occurrence of intermediate-sized filaments of the vimentin-type in cultured cells from diverse vertebrates. *Exp Cell Res* 123, 25 (1979).
21. S. Di Bartolomeo et al., The dynamic interaction of AMBRA1 with the dynein motor complex regulates mammalian autophagy. *J Cell Biol* 191, 155 (2010).
22. Larance et al. Global Phosphoproteomics Identifies a Major Role for AKT and 14-3-3 in Regulating EDC3* *Molecular & Cellular Proteomics* 9.4, 682-694 (2010).

2. EGFR-Mediated Beclin 1 Phosphorylation in Autophagy Suppression, Tumor Progression and Tumor Chemoresistance Cell surface growth factor receptors couple environmental cues to the regulation of cytoplasmic homeostatic process including autophagy, and aberrant activation of such receptors is a common feature of human malignancies. Here, we defined the molecular basis by which the epidermal growth factor receptor (EGFR) tyrosine kinase regulates autophagy. Active EGFR binds to the autophagy protein Beclin 1, leading to its multisite tyrosine phosphorylation, enhanced binding to inhibitors, and decreased Beclin 1-associated Class III phosphatidylinositol-3 kinase activity. EGFR tyrosine kinase inhibitor (TKI) therapy disrupts Beclin 1 tyrosine phosphorylation and binding to its inhibitors, and restores autophagy in non-small cell lung carcinoma (NSCLC) cells with a TKI-sensitive EGFR mutation. In NSCLC tumor xenografts, the expression of a tyrosine phosphomimetic Beclin 1 mutant leads to reduced autophagy, enhanced tumor growth, tumor dedifferentiation, and resistance to TKI therapy. Thus, oncogenic receptor tyrosine kinases directly regulate the core autophagy machinery, which can contribute to tumor progression and chemoresistance.

In this example we disclose, inter alia, that: (a) EGFR negatively regulates autophagy by binding to Beclin 1; (b) active EGFR phosphorylates Beclin 1 and alters its interactome; (c) EGFR suppression of Beclin 1 contributes to tumor progression in lung cancer; and (d) lung cancer responses to EGFR inhibitors involve activation of Beclin 1

Introduction

Epidermal growth factor receptor (EGFR), an oncogenic receptor tyrosine kinase, links extracellular signals to cellular homeostasis. In normal cells, EGFR signaling is triggered by the binding of growth factors, such as epidermal growth factor (EGF), leading to homodimerization or heterodimerization with other EGFR family members (such as HER2/neu) and autophosphorylation of the intracellular domain (Lemmon and Schlessinger, 2010). The phosphotyrosines formed serve as a docking site for adaptor molecules, which results in the activation of signaling pathways including the Ras/MAPK pathway, the PI3K/Akt pathway, and STAT signaling pathways. In tumor cells, the tyrosine kinase activity of EGFR may be dysregulated by EGFR gene mutation, increased EGFR gene copy number, or EGFR protein overexpression, leading to aberrant EGFR signaling and increased tumor cell survival, proliferation, invasion and metastasis (Ciardiello and Tortora, 2008). EGFR signaling is deregulated in many human cancers, including those of the lung, head and neck, colon, pancreas, and brain.

The deregulation of EGFR in human cancers has led to the development of anticancer agents that target EGFR, including: (1) anti-EGFR antibodies that inhibit ligand binding: and (2) small molecule receptor tyrosine kinase inhibitors (TKIs), erlotinib and gefitinib, that block EGFR intracellular tyrosine kinase activity. Although the EGFR TKIs have shown limited clinical benefit in the majority of solid tumors, they are effective in non-small lung carcinomas (NSCLCs) that harbor specific mutations in the tyrosine kinase domain of EGFR (most commonly, in-frame deletion in exon 19 around codons 746-750 or single-base substitution, L858R, in exon 21) (Ciardiello and Tortora, 2008; Lynch et al., 2004; Pao and Chmielecki, 2010). Most patients with NSCLCs with EGFR mutations initially respond favorably to erlotinib or gefitinib, suggesting these mutations drive tumorigenesis. However, among tumors that initially respond to EGFR TKIs, most eventually acquire resistance, often due to the emergence of a secondary mutation, T790M, in the kinase domain of EGFR (Pao and Chmielecki, 2010).

Several studies have shown that EGFR signaling regulates autophagy, a lysosomal degradation pathway that functions in cellular homeostasis and protection against a variety of diseases, including cancer (Levine and Kroemer, 2008). The downstream targets of EGFR—PI3K, Akt, and mTOR—are well-established negative regulators of autophagy (Botti et al., 2006). Moreover, EGFR inhibitors induce autophagy in NSCLCs (Gorzalczany et al., 2011; Han et al., 2011) and other cancer cells (Fung et al., 2012). However, the links between EGFR signaling and autophagy remain poorly understood, particularly (1) the molecular mechanisms by which EGFR signaling suppresses autophagy; (2) the role of EGFR suppression of autophagy in lung cancer pathogenesis; and (3) the role of autophagy induction in the response to TKI therapy. EGFR inhibitor-induced autophagy in lung cancer cells has been postulated to exert either cytoprotective (Han et al., 2011) or cytotoxic (Gorzalczany et al., 2011) effects.

Conflicting results regarding the role of autophagy in the response or resistance to EGFR TKI treatment reflects broader uncertainties in the role of autophagy in cancer therapy (Rubinsztein et al., 2012). It is not understood in what contexts autophagy induction contributes to tumor progression or suppression and to tumor chemoresistance or chemosensitivity. There is a general consensus that autophagy prevents tumor initiation, as loss-of-function mutations of several different autophagy genes results in spontaneous tumorigenesis (beclin 1, Atg5, Atg7) and/or increased chemical-induced tumorigenesis (Atg4C) in mice (Rubinsztein et al., 2012). Despite this inhibitory role in tumor initiation, it has been proposed that autophagy may promote the growth of established tumors and contribute to chemoresistance, principally through its actions to prolong the survival of metabolically-stressed neoplastic cells (Rubinsztein et al., 2012).

To understand the relationship between oncogenic signaling, autophagy, and distinct stages of tumorigenesis, it is important to define the molecular mechanisms by which oncogenic signaling regulates autophagy. We recently showed that the oncogene Akt inhibits autophagy independently of mTOR signaling via serine phosphorylation of the essential autophagy protein, Beclin 1 (Wang et al., 2012), a haploinsufficient tumor suppressor protein frequently monoallelically deleted in human breast and ovarian cancer (Levine and Kroemer, 2008). Moreover, Akt-mediated phosphorylation of Beclin 1 contributes to Akt-dependent fibroblast transformation, supporting the concept that inactivation of Beclin 1-dependent autophagy plays a role in tumor initiation. However, it is not known whether oncogenic inactivation of Beclin 1 (or other autophagy proteins) influences progression of established tumors and/or their response to therapy.

Here we identify the molecular basis by which EGFR tyrosine kinase activity regulates autophagy. We show that active EGFR binds to Beclin 1, leading to its tyrosine phosphorylation, alteration of its interactome, and inhibition of its autophagy function. A mutant of Beclin 1 containing phosphomimetic mutations in the EGFR-dependent tyrosine phosphorylation sites enhances autophagy suppression in EGFR-mutated NSCLC cells, resulting in enhanced tumor progression, altered tumor cell differentiation, and partial tumor resistance to EGFR TKI therapy. These findings demonstrate a heretofore unknown link between oncogenic receptor tyrosine kinases and the autophagy machinery, which can contribute to tumor progression and resistance to targeted therapy.

Results

EGFR Activation Promotes Autophagy Inhibition and EGFR/Beclin 1 Complex Formation.

To evaluate whether EGFR activation inhibits autophagy, we used a human non-small cell lung carcinoma (NSCLC) cell line, A549, that express wild-type (WT) EGFR (VanMeter et al., 2008). We measured autophagy by examining the subcellular localization of a green fluorescent autophagy reporter protein, GFP-LC3, and by measuring levels of LC3-II, the autophagosome-associated lipidated form of LC3, and p62, an autophagic substrate (Mizushima et al., 2010). Serum depletion resulted in marked autophagy induction, as evidenced by an increase in GFP-LC3 puncta (autophagosomes) per cell, increased LC3-II conversion, and increased p62 degradation. EGF addition to the serum-starved cells for 30 min partially reversed autophagy induction.

To determine the mechanism by which EGFR activation inhibits autophagy, we investigated whether the EGFR can interact with Beclin 1, a component of the Class III phosphatidylinositol 3-kinase (PI3K) (VPS34) autophagy-inducing complex. During growth in normal or serum-free media when no EGFR phosphorylation was observed, EGFR did not co-immunoprecipitate with Beclin 1. However, when cells were treated with EGF and EGFR was phosphorylated, EGFR co-immunoprecipitated with Beclin 1. Thus, active phosphorylated EGFR interacts with a key component of the autophagy machinery, Beclin 1, in human NSCLC cells in a ligand-dependent manner.

The EGFR is a cell surface receptor that undergoes ligand-dependent dimerization, phosphorylation of tyrosine residues within its cytoplasmic tail, and endocytosis (Lemmon and Schlessinger, 2010). We examined the colocalization of WT EGFR and Beclin 1 in A549 cells stably expressing Flag-Beclin 1. In the absence of EGF stimulation, almost all EGFR localized to the cell surface and did not colocalize with Flag-Beclin 1. In contrast, after EGF stimulation, EGFR was observed in punctate intracellular vesicles and colocalized with Flag-Beclin 1. This colocalization required EGFR endocytosis, and not just receptor homodimerization, as inhibition of EGFR endocytosis by clathrin siRNA blocked EGFR and Beclin 1 colocalization in EGF-treated A549 cells. To determine the identity of the intracellular vesicles with EGFR immunostaining, we evaluated the colocalization of EGFR with different organelle markers, including EEA1 (an early endosome marker), LAMP1 (a late endosome/lysosome marker) and Tom20, a mitochondrial marker. Internalized EGFR colocalized with EEA1, indicating that the majority of active EGFR resides in endosomes. We also observed weak colocalization of EGFR with LAMP1 and Tom20, consistent with the lysosomal trafficking of endocytosed wild-type EGFR (Carpenter, 1987) and its reported mitochondrial localization (Yao et al., 2010).

Together, these data indicate that ligand-dependent EGFR activation leads to the interaction of EGFR and Beclin 1.

Active EGFR Mutants Interact with Beclin 1 and Inhibit Autophagy Independently of mTOR.

To further evaluate whether ligand-dependent and -independent activation of EGFR results in the formation of an EGFR/Beclin 1 complex and autophagy suppression, we used HeLa cells which express low levels of endogenous EGFR. HeLa cells were transfected either with WT EGFR, which requires EGF stimulation for EGFR phosphorylation and activation, or with constitutively active mutants of EGFR. WT EGFR co-immunoprecipitated with Flag-Beclin 1 only when activated (tyrosine phosphorylated) by EGF stimulation. In contrast, an active EGFR mutant common in NSCLCs, EGFR L858R, co-immunoprecipitated with Flag-Beclin 1 in the absence of EGF stimulation. The TKI, erlotinib, which binds to the EGFR ATP binding site, dephosphorylated EGFR and abolished the EGFR/Beclin 1 interaction. Similar results were also observed with another active mutant EGFR, EGFRΔ746-750, also commonly found in NSCLC patients. Thus, both ligand-dependent stimulation of WT EGFR and activating mutations in EGFR associated with NSCLC promote the formation of an EGFR/Beclin 1 complex.

We investigated the effects of active EGFR mutants that constitutively bind Beclin 1 on autophagy. Both amino acid starvation and the ATP-competitive inhibitor of mTOR, Torin1, induced autophagy in HeLa cells transfected with empty vector or WT EGFR. In cells transfected with the active EGFR mutants, L858R or 4746-750, starvation and Torin1 induced lower levels of autophagy. However, active EGFR did not block either starvation- or Torin1-induced mTOR deactivation. Thus, active EGFR mutants suppress autophagy in a manner that is partially independent of mTOR.

Active EGFR Mutants and EGF-Stimulation of Wild-Type EGFR Alter the Beclin 1 Interactome The results above indicated that the EGFR/Beclin 1 interaction can alter the Beclin 1-containing autophagy-inducing Class III PI3K complex. We mapped the EGFR binding domains of Beclin 1 in HeLa cells co-transfected with the active EGFR L858R mutant and Beclin 1 truncation mutants Amino acids 1-135 but not 1-115 of Beclin 1 co-immunoprecipitated with active EGFR, suggesting that amino acids 115-135 containing the BH3 domain contribute to the interaction between Beclin 1 and EGFR. In addition, the evolutionarily conserved domain (ECD) of Beclin 1 spanning from amino acids 244-377 was sufficient to bind EGFR. Thus, Beclin 1 contains at least two domains (the BH3 domain and the ECD domain) capable of binding to EGFR.

We hypothesized that EGFR binding enhances the interaction of Beclin 1 with negative regulators such as Bcl-2 (which binds to the Beclin 1 BH3 domain) and Rubicon (which binds to the Beclin 1 ECD) and diminishes the interaction of Beclin 1 with VPS34, the Class III PI3K involved in autophagosome initiation (which binds to the Beclin 1 ECD) (He and Levine, 2010). Therefore, we examined the effects of expression of WT and active mutant EGFRs in HeLa cells on the interaction between Beclin and its binding partners, Bcl-2, Rubicon, VPS34, UVRAG and ATG14. Active EGFR did not influence the interaction between Beclin 1 and ATG14 or Beclin 1 and UVRAG. However, expression of either of the active EGFR mutants (L858R or Δ746-750) increased co-immunoprecipitation of Beclin 1 and Rubicon and of Beclin 1 and Bcl-2. Conversely, cells expressing either of the active EGFR mutants had decreased co-immunoprecipitation of Beclin 1 and VPS34. This EGFR-regulated alteration in the Beclin 1 interactome was associated with decreased Beclin 1-associated VPS34 kinase activity. EGF stimulation resulted in similar alterations in the Beclin 1 interactome and a similar decrease in Beclin 1-associated VPS34 kinase activity in A549 NSCLC cells that express WT EGFR. Together, these data indicate that binding of EGFR to Beclin 1 (either via ligand-dependent EGFR activation or via activating mutations in EGFR) suppresses autophagy by regulating the Beclin 1 interactome.

EGFR-Dependent Regulation of Autophagy and Beclin 1 Complex Formation in NSCLC Cells with Active EGFR Mutants We investigated whether this mechanism underlies EGFR regulation of autophagy in NSCLC cells with activating mutations in EGFR. We used two NSCLC lines: HCC827 cells have the Δ746-750 EGFR activating mutation and are TKI-sensitive, and H1975 cells have the L858R EGFR activating mutation and are TKI-resistant due to a T790M mutation. First, we evaluated if TKI treatment induces autophagy; erlotinib blocked the Beclin 1/EGFR interaction and increased GFP-LC3 puncta in a dose-dependent manner in TKI-sensitive HCC827 cells stably transfected with GFP-LC3 but not in TKI-resistant H1975 cells stably transfected with GFP-LC3. Furthermore, HCC827 cells but not H1975 cells demonstrated LC3-II conversion and p62 degradation after erlotinib treatment. Thus, TKI therapy disrupts the EGFR/Beclin 1 complex and induces autophagy in TKI-sensitive but not TKI-resistant cells. This association between TKI sensitivity and autophagy induction was also observed in vivo in tumor xenografts formed by HCC827/GFP-LC3 and H1975/GFP-LC3 cells; HCC827/GFP-LC3 xenografts had increased autophagosomes after TKI treatment and underwent complete regression within several days, whereas H1975/GFP-LC3 xenografts did not have increased autophagosomes and failed to respond to TKI treatment.

Since erlotinib decreased mTOR activity in HCC827 cells, as measured by phosphorylation of the mTOR substrate, 4E-BP1, we asked if erlotinib-induced autophagy is dependent on suppression of mTOR. We transfected HCC827 cells with a constitutively active mTOR mutant S2215Y (Sato et al., 2010) that blocks starvation-induced mTOR deactivation and dephosphorylation of 4E-BP1. mTOR S2215Y expression in HCC827 cells decreased levels of erlotinib-induced mTOR and 4E-BP1 dephosphorylation but had no effect on erlotinib-induced autophagy.

Thus, TKI-induced autophagy in a NSCLC cell line with an active EGFR mutation is independent of mTOR deactivation.

We investigated whether TKI-induced autophagy in HCC827 cells involves regulation of the Beclin 1 interactome. In TKI-sensitive HCC827 cells (but not in TKI-resistant H1975 cells), erlotinib led to EGFR dephosphorylation, disruption of EGFR/Beclin 1 binding, disruption of Beclin 1/Rubicon binding, increased Beclin 1/VPS34 binding, decreased Beclin 1/Bcl-2 binding, and increased Beclin 1-associated VPS34 kinase activity. Thus, TKI-induced autophagy in NSCLCs with active EGFR is associated with increased Beclin 1-associated VPS34 kinase activity and disruption of the interaction between Beclin 1 and EGFR and between Beclin 1 and negative regulators of autophagy such as Bcl-2 and Rubicon. The effect of active EGFR on Beclin 1/Bcl-2 and Beclin 1/VPS34 interactions is likely indirect, as only Beclin 1 and Rubicon (but not Bcl-2, ATG14, UVRAG, or VPS34) co-immunoprecipitate with active EGFR in HCC827 cells.

Mutational Activation of EGFR and Ligand Stimulation of Wild-Type EGFR Results in Beclin 1 Tyrosine Phosphorylation We investigated whether regulation of Beclin 1 function by active EGFR involves Beclin 1 tyrosine phosphorylation. Beclin 1 was tyrosine phosphorylated in NSCLC cells with WT EGFR after EGF stimulation and in NSCLC cells with active EGFR mutations (HCC827 and H1975 cells). This was decreased by erlotinib in TKI-sensitive HCC827 cells but not TKI-resistant H1975 cells Inhibition of c-Met, another oncogenic receptor tyrosine kinase activated in HCC827 cells, did not block Beclin 1 tyrosine phosphorylation, and Beclin 1 did not co-immunoprecipitate with active c-Met. This indicates that active EGFR (but not other receptor tyrosine kinases) is responsible for Beclin 1 tyrosine phosphorylation in HCC827 cells.

We identified sites of EGFR-mediated in vitro Beclin 1 phosphorylation using recombinant active EGFR L858R/T790M and two synthetic peptides derived from regions of Beclin 1 containing three database-identified candidate tyrosine phosphorylation sites, Y229, Y233 and Y352. Active EGFR phosphorylated the Beclin 1 peptide spanning amino acids 223-239 in a concentration-dependent manner, while control tyrosine kinases, including PDGFRβ, mutationally active PDGFRα T674I and SRMS, did not. Mutation of both Y229 and Y233 was required to block EGFR-dependent phosphorylation of the Beclin 1 amino acid 223-239 peptide. The peptide spanning Y352 (Beclin 1 amino acids 345-358) underwent low levels of phosphorylation at the highest peptide concentration examined. Thus, Beclin 1 Y229, Y233, and possibly Y352 are substrates of EGFR-mediated Beclin 1 tyrosine phosphorylation.

To evaluate whether Beclin 1 Y229, Y233 and/or Y352 are required for Beclin 1 tyrosine phosphorylation in HCC827 NSCLC cells, we expressed Flag epitope-tagged WT and mutant Beclin 1 constructs. While the peptide spanning Beclin 1 Y352 was only mildly phosphorylated by active EGFR in vitro, simultaneous mutation of all three candidate tyrosine phosphorylation sites (Y229F, Y233F and Y352F) in full-length Beclin 1 was required to block Beclin 1 tyrosine phosphorylation. Thus, in NSCLC cells with active EGFR, three Beclin 1 tyrosine residues—Y229, Y233 and Y352—are phosphorylated. These residues are conserved in Beclin 1 throughout metazoan evolution.

Flag-Beclin 1 Y233 phosphorylation was detected in HCC827 cells transfected with WT Flag-Beclin 1 but not with mutant Flag-Beclin 1 Y233F using a phosphospecific antibody. Endogenous Beclin 1 Y233 phosphorylation was detected in A549 cells expressing WT EGFR after EGF stimulation and in HCC827 and H1975 cells with active EGFR mutations. This phosphorylation was blocked by erlotinib in HCC827 but not in H1975 cells. Thus, Beclin 1 Y233 phosphorylation is regulated by ligand-dependent and ligand-independent activation of EGFR. Furthermore, NSCLC cells with activating mutations in EGFR (H1975, H3255 and HCC827) had detectable Beclin 1 Y233 phosphorylation, whereas cells with amplified wild-type EGFR (A549, H1703, H1819 and H2073), with amplified c-Met (H1933) or with K-Ras mutation (HCC4017, H2122) did not, indicating that Beclin 1 Y233 phosphorylation is a specific marker of mutationally active EGFR in NSCLC.

To evaluate the functional consequences of Beclin 1 tyrosine phosphorylation, we generated NSCLC cells that stably express WT Flag-Beclin 1 or Flag-Beclin 1 containing three non-phosphorylatable mutations, Y229F/Y233F/Y352F (FFF) or three phosphomimetic mutations, Y229E/Y233E/Y352E (EEE). Flag-Beclin 1 FFF interacted with active EGFR and its interactome was regulated by EGFR inhibition in a manner similar to that of WT Flag-Beclin 1. This most likely reflects the presence of endogenous Beclin 1 in these cells (which is tyrosine phosphorylated when EGFR is active) and the homodimerization of Beclin 1 FFF with WT Beclin 1, as Beclin 1 homodimerization is predicted to favor binding to Rubicon and Bcl-2 and disfavor binding to VPS34. In contrast, the phosphomimetic Beclin 1 EEE mutant escaped regulation by TKI treatment; erlotinib resulted in dephosphorylation of EGFR (indicating preserved receptor sensitivity to TKIs) but did not disrupt Beclin 1 EEE/EGFR, Beclin 1 EEE/Rubicon, or Beclin 1/Bcl-2 interactions, and did not increase the Beclin 1 EEE/VPS34 interaction or increase Beclin 1 EEE-associated VPS34 kinase activity. In addition, unlike WT Beclin 1 or Beclin 1 FFF, the Beclin 1 EEE mutant dimerized with itself or with WT Beclin 1 in HCC827 cells in the setting of EGFR inhibition. Together, these findings indicate that the Beclin 1 EEE mutant mimics tyrosine phosphorylated Beclin 1.

Perhaps via constitutive dimerization with endogenous WT Beclin 1, Beclin 1 EEE functioned as a dominant negative mutant of TKI-induced autophagy. Despite the presence of endogenous Beclin 1 in NSCLC cells, overexpression of Beclin 1 EEE suppressed erlotinib-induced autophagy. Thus, Beclin 1 tyrosine dephosphorylation (and disruption of Beclin 1 homodimerization) may be essential for TKI-induced autophagy. Moreover, a lower level of basal autophagy and Beclin 1-associated VPS34 kinase activity was observed in non-TKI-treated HCC827 cells expressing Beclin 1 EEE. This indicates that constitutive Beclin 1 tyrosine phosphorylation enhances autophagy suppression in cells with active EGFR mutation.

A Beclin 1 Tyrosine Phosphomimetic Mutant Enhances Autophagy Suppression, Tumor Growth, and Tumor Dedifferentiation of NSCLC Xenografts As Beclin 1 EEE expression in NSCLC cells enhanced autophagy suppression in vitro, we evaluated the effects of Beclin 1 EEE expression on NSCLC autophagy and tumor progression in vivo, using a SCID/NOD mouse xenograft model. Beclin 1 EEE-expressing NSCLC xenografts had lower levels of autophagy, and grew at a faster rate than those derived from NSCLCs transfected with empty vector control, WT Beclin 1, or Beclin 1 FFF. Conversely, although there was no difference in tumor volume on day 35, xenografts from NSCLCs expressing either WT Beclin 1 or Beclin 1 FFF grew at a slower rate than control xenografts and had biochemical evidence of increased autophagy. Thus, in human NSCLC xenografts with EGFR mutation, changes in autophagic activity are associated with inverse changes in the rates of tumor growth.

This inverse relationship seemingly contradicts the paradigm that autophagy fosters the growth of established tumors (Amaravadi et al., 2011; Rubinsztein et al., 2012). This pro-tumor function of autophagy is thought to be related to its role in promoting cell survival in the metabolically stressed tumor microenvironment, and indeed, we found that NSCLC xenografts with increased autophagy had decreased cell death. NSCLC xenografts with overexpression of WT Flag-Beclin 1 or mutant Flag-Beclin 1 FFF (which increased steady-state levels of autophagy) had decreased numbers of TUNEL-positive cells, whereas NSCLC xenografts with overexpression of mutant Flag-Beclin 1 EEE (which suppressed steady-state levels of autophagy) had increased numbers of TUNEL-positive cells. Thus, although autophagy exerts pro-survival effects in established tumors, the amount of autophagy-dependent cell survival may be insufficient to determine tumor growth in NSCLC.

We observed other differences that may account for increased tumor growth in NSCLC xenografts expressing the Beclin 1 tyrosine phosphomimetic mutant. NSCLC xenografts expressing Beclin 1 EEE exhibited increased cell proliferation. Consistent with this increased proliferation, NSCLC xenografts expressing Beclin 1 EEE also had an increase in variance of nuclear DNA intensity, perimeter, and area. More entotic (cell-in-cell structures) and more multinucleated cells were also observed in NSCLC xenografts expressing Beclin 1 EEE. This increase in entotic and multinucleated cells was not associated with an increase in variance in DNA ploidy in cells with single nuclei, although NSCLC xenografts expressing WT Beclin 1 or Beclin 1 FFF (which had increased levels of autophagy) had a decreased variance in DNA ploidy.

In addition to the aforementioned features, histopathologic analyses revealed significant morphologic differences in NSCLCs xenografts expressing Beclin 1 EEE. HCC827 cells were derived from 39 year-old never-smoking woman with primary lung adenocarcinoma (Gazdar and Minna, 1996), and xenografts from control HCC827 cells, HCC827/Flag-Beclin 1, and HCC/Flag-Beclin 1 FFF cells displayed characteristic features of lung adenocarcinomas with mutated EGFR (Shim et al., 2011). They manifested varying degrees of gland formation and cohesive clusters of pleomorphic epithelial cells (admixed with clusters of smaller ovoid or spindle-shaped cells). In contrast, HCC827/Flag-Beclin 1 EEE xenografts appeared more poorly differentiated; they lacked overt glandular differentiation, had more infiltrative features, and tumor infiltrates often exhibited a solid growth pattern with morphologic characteristics suggesting squamous differentiation i.e. large cells with centrally placed nuclei and increased amounts of pale pink cytoplasm (low nucleus-cytoplasmic ratio). No differences were observed among the NSCLC xenograft groups in terms of immunostaining for the markers of epithelial to mesenchymal transition, e-cadherin and vimentin.

To confirm the change in differentiation status of HCC827/Flag-Beclin 1 EEE tumors, we stained all xenografts for TTF-1, p63, and cytokeratin 5 (CK5), which are used clinically to distinguish between lung adenocarcinoma and squamous carcinoma (Rekhtman et al., 2011). All xenografts had diffuse low expression of p63 (a marker of squamous differentiation, but also expressed by many lung adenocarcinomas) and lacked expression of CK5 (a marker of squamous cell carcinoma). In contrast, marked differences were observed in expression of TTF-1, a homeodomain protein that is highly expressed in lung adenocarcinomas and whose loss of expression is associated with aggressive tumor behavior and decreased median survival in patients with NSCLC (Saad et al., 2004; Tang et al., 2011). All control HCC827, HCC827/Flag-Beclin 1, and HCC827/Flag-Beclin 1 FFF xenografts displayed strong TTF-1 staining homogenously in nearly all tumor cells, while the majority of tumor cells in HCC827/Flag-Beclin 1 EEE xenografts displayed either weak or undetectable TTF-1 staining. Using an established pathological score for grading TTF-1 staining (Saad et al., 2004), 10/10 xenografts were strongly positive in the control HCC827, HCC827/Flag-Beclin 1, and HCC827/Flag-Beclin 1 FFF groups, whereas 7/10 xenografts were weakly positive and 3/10 xenografts were moderately positive in the HCC827/Flag-Beclin 1 EEE group.

Thus, expression of a Beclin 1 tyrosine phosphomimetic in NSCLC xenografts in mice results in decreased autophagy, increased cellular proliferation, accelerated tumor growth, and dedifferentiation from TTF-1-positive adenocarcinomas to TTF-1-negative poorly differentiated tumors with features of squamous differentiation. This phenotype is analogous to human adenosquamous carcinoma, an NSCLC subtype associated with a worse prognosis. Similar findings were observed in NSCLC xenografts from three independent Beclin 1 EEE clones, indicating that their aggressive features do not represent a clonal artifact.

Inhibition of TKI-Induced Autophagy in NSCLC Xenografts Results in Resistance to TKI Therapy We evaluated the effects of blocking TKI-mediated autophagy on the response of NSCLCs to TKI therapy. Since constitutive Beclin 1 EEE expression alters the natural history of HCC827 xenografts, we generated HCC827 cell lines that express tetracycline-inducible WT Beclin 1 or Beclin 1 Y229E/Y233E/Y352 (EEE) to induce protein expression in established tumors immediately prior to initiation of TKI therapy. We confirmed that doxycycline induction of Beclin 1 EEE expression (but not of WT Beclin 1) in HCC827 cells reduced levels of erlotinib-induced autophagy. The suppression of erlotinib-induced autophagy by Beclin 1 EEE expression was associated with an increase in clonogenic survival of HCC827 cells after treatment with erlotinib. A similar increase in clonogenic survival was also observed in erlotinib-treated HCC827 cells with ATG7 siRNA knockdown, indicating that autophagy suppression, rather than other potential effects of Beclin 1 EEE expression, contributes to TKI-resistance. Similarly, selective inhibition of autophagy (without inhibition of apoptosis) by a mutant viral Bcl-2 (M11 AAA) protein that binds to Beclin 1 but not Bax increased HCC827 clonogenic survival following treatment with erlotinib.

We confirmed that these effects of autophagy suppression in vitro on NSCLC resistance to TKI therapy also occurred in vivo, using xenografts derived from HCC827 cells expressing tetracycline-inducible Beclin 1 EEE and from HCC827 cells expressing the mutant viral Bcl-2 protein. In HCC827 xenografts, induced expression of Beclin 1 EEE decreased numbers of autophagosomes one day after initiation of erlotinib and resulted in partial resistance to erlotinib. In untreated control mice and in mice with induced expression of WT Beclin 1, there was complete regression of all tumor xenografts within 14 days. In contrast, xenografts with induced expression of Beclin 1 EEE had a slower rate of tumor regression and all tumors remained at the end of the 28-day observation period. Similarly, xenografts derived from HCC827 cells expressing the viral Bcl-2 inhibitor of autophagy had decreased erlotinib-induced autophagy and were partially resistant to erlotinib. Together, these results indicate that Beclin 1 tyrosine phosphorylation and autophagy suppression contribute to TKI resistance in NSCLCs with EGFR mutations.

Discussion

Active EGFR Suppresses Autophagy Through Beclin 1 Tyrosine Phosphorylation

Here we demonstrate that upon activation, EGFR interacts with Beclin 1, promoting its tyrosine phosphorylation and inactivation. This effect occurs in cells expressing WT EGFR upon EGF binding as well as in human NSCLC cells with activating cancer-driving mutations in EGFR. Thus, EGFR signaling suppresses autophagy via its interaction with Beclin 1 during normal mitogenic signaling as well as during aberrant cell proliferation in cancer cells.

These findings directly link receptor tyrosine kinases involved in cell growth control and autophagy suppression. Several downstream molecules in the EGFR signaling pathway, including PI3K, Akt and mTOR, are known to negatively regulate autophagy (Botti et al., 2006). Our results uncover a new mechanism of EGFR suppression of autophagy that is mTOR independent—involving an interaction between EGFR and the Beclin 1 autophagy protein—which underscores the importance of autophagy suppression by EGFR signaling. While we did not find evidence of EGFR-independent Beclin 1 tyrosine phosphorylation in NSCLC cells with active EGFR mutations, other members of the EGFR family (e.g. HER2, HER3, HER4) and/or other oncogenic receptor tyrosine kinases may also inactivate Beclin 1 and the autophagy pathway in other cell types.

The mechanism by which EGFR suppresses Beclin 1 function involves EGFR interaction with two domains (BH3 and ECD) of Beclin 1; EGFR-mediated multisite tyrosine phosphorylation of Beclin 1 on residues Y229, Y233 and Y352; and EGFR-mediated alterations in the Beclin 1 interactome (increased binding to the negative regulators, Bcl-2 and Rubicon, and decreased binding to the VPS34 lipid kinase). The interaction between EGFR and Beclin 1 most likely occurs in endosomes, the site of EGFR signaling following ligand-dependent internalization (with WT EGFR) and of kinase domain mutants that promote constitutive activation and constant endocytic internalization (Wang et al., 2002). Active EGFR interacts with Beclin 1 and Rubicon, but not other Beclin 1 binding partners, such as Bcl-2, VPS34, UVRAG, or ATG14. Thus, the regulation of the Beclin 1 interactome (increased Beclin 1/Bcl-2 binding and decreased Beclin 1/VPS34 binding) by EGFR-mediated phosphorylation is indirect. Our data showing that Beclin 1 tyrosine phosphorylation promotes Beclin 1 homodimerization indicates a model (supported by the crystal structures of the Beclin 1 coiled coil region and evolutionarily conserved domain) in which EGFR-mediated Beclin 1 tyrosine phosphorylation favors the formation of Beclin 1 dimers that are unable to bind VPS34 and promote autophagy. In addition to blocking autophagy, EGFR-mediated Beclin 1 tyrosine phosphorylation may also block its own endolysosomal degradation by promoting the binding of Rubicon to tyrosine phosphorylated Beclin 1, as Rubicon inhibits EGF-stimulated EGFR degradation in A549 cells (Matsunaga et al., 2009). Thus, activating mutations in EGFR can exert multiple effects on Beclin 1; EGFR-dependent Beclin 1 tyrosine phosphorylation can both suppress its autophagy activity as well as its role in endolysosomal trafficking.

EGFR Suppression of Beclin 1 May Contribute to Tumor Progression in Non-Small Cell Lung Carcinoma Several lines of evidence indicate that decreased Beclin 1 function contributes to tumor initiation: allelic loss of Beclin 1 increases the incidence of spontaneous malignancies in mice; Akt-mediated phosphorylation of Beclin 1 contributes to Akt-fibroblast transformation; and allelic loss of Beclin 1 in immortalized mammary epithelial cell lines enhances their tumorigenesis in vivo (Levine and Kroemer, 2008; Wang et al., 2012). However, to date, it has been unclear whether loss of Beclin 1 function contributes to the progression of established tumors. Our present findings indicate that enhanced Beclin 1 inactivation (via constitutive expression of a tyrosine phosphomimetic mutant) augments tumor growth of existing NSCLCs with active EGFR mutation. In addition to accelerated growth and increased cell proliferation, tumors with expression of the Beclin 1 tyrosine phosphomimetic have histopathologic features indicative of a de-differentiated, more aggressive neoplasm, including squamous differentiation, increased infiltration, and loss of TTF-1 expression. Since activating EGFR mutations in NSCLC result in constitutive Beclin 1 tyrosine phosphorylation, endogenous Beclin 1 tyrosine phosphorylation in NSCLCs can similarly contribute to tumor progression.

We observed decreased cell death in NSCLCs with increased autophagy (i.e. those overexpressing WT Beclin 1 or a non-phosphorylatable mutant of Beclin 1, Beclin 1 Y229F/Y233F/Y352F), and we observed increased cell death in NSCLCs with decreased autophagy (i.e. those overexpressing a tyrosine phosphomimetic mutant of Beclin 1, Beclin 1 Y229E/Y233E/Y352E). These results are consistent with previous studies demonstrating that autophagy functions as a pro-survival pathway in the metabolically stressed tumor microenvironment (Amaravadi et al., 2011; Rubinsztein et al., 2012). However, at least in NSCLCs, the amount of cell death may not be the primary determinant of tumor progression. Other previously described anti-tumor functions of autophagy such as preventing DNA damage and chromosomal instability, and limiting cell proliferation (Levine and Kroemer, 2008) and/or other effects of Beclin 1 such as the prevention of tumor dedifferentiation, may prevail over the pro-survival effects of autophagy in limiting tumor progression. Our observation that tumors with the least autophagy and the greatest amount of cell death also were the most aggressive (in terms of growth rate and histopathology) raise important questions about the strategy of inhibiting autophagy in cancer simply because it can function as a pro-survival pathway. Although such strategies may increase tumor cell death, they may promote tumor progression by blocking other autophagy-dependent functions.

NSCLC Response to EGFR TKI Therapy May Involve Activation of Beclin 1 and Autophagy Our results have direct implications for the treatment of patients with active EGFR mutations and non-small cell lung carcinoma. Based on previous data that EGFR TKIs induce autophagy (Gorzalczany et al., 2011; Han et al., 2011) and the belief that autophagy induction may lead to chemoresistance (Amaravadi et al., 2011), there are currently several NIH-sponsored clinical trials that combine autophagy inhibitory agents (e.g. chloroquine and hydoxychloroquine) with EGFR inhibitors in the treatment of NSCLC. Earlier studies have either claimed that autophagy induction can enhance or limit the response to EGFR TKI therapy, but they suffer from experimental limitations, including (1) the use of NSCLC cell lines with WT EGFR or overexpressed EGFR rather than NSCLCs with TKI-sensitive mutations in EGFR (which are the tumors that clinically respond best to TKI therapy); (2) induction of autophagy with the use of high doses of TKIs, which are not relevant to those prescribed to patients; (3) the use of assays based on mitochondrial activity (which reflect both cell proliferation and death) rather than clonogenic survival assays to determine the effect of autophagy manipulation on NSCLC survival; and most importantly (4) the lack of in vivo studies that directly assess the effects of modulating autophagy on the response of NSCLC to TKIs. By contrast, we assessed clonogenic survival of NSLCs cells with an active mutation in EGFR after treatment with a clinically relevant concentration of erlotinib using three complementary approaches to inactivate erlotinib-induced autophagy: expression of a Beclin 1 tyrosine phosphomimetic, expression of a viral Bcl-2 mutant that selectively inhibits autophagy but not apoptosis, and siRNA knockdown of an autophagy gene ATG7 that functions downstream of Beclin 1. In all these studies, autophagy inhibition was associated with increased clonogenic survival and TKI resistance in vitro. Moreover, in tumor xenografts formed by TKI-sensitive NSCLC cells, TKI resistance was conferred either by expression of a viral Bcl-2 autophagy inhibitor or inducible expression of the Beclin 1 tyrosine phosphomimetic mutant that blocks autophagy. Together, our data indicate that (1) autophagy induction contributes to EGFR TKI responses in NSCLCs with active EGFR mutations; and (2) the use of autophagy inhibitors in patients receiving EGFR TKIs can adversely affect their clinical course.

REFERENCES

Amaravadi, R. K., Lippincott-Schwartz, J., Yin, X. M., Weiss, W. A., Takebe, N., Timmer, W., DiPaola, R. S., Lotze, M. T., and White, E. (2011). Principles and current strategies for targeting autophagy for cancer treatment. Clin. Cancer Res. 17, 654-666.

Botti, J., Djavaheri-Mergny, M., Pilatte, Y., and Codogno, P. (2006). Autophagy signaling and the cogwheels of cancer. Autophagy 2, 67-73.

Carpenter, G. (1987). Receptors for epidermal growth factor and other polypeptide mitogens. Annu. Rev. Biochem. 56, 881-914.

Ciardiello, F., and Tortora, G. (2008). EGFR antagonists in cancer treatment. N. Engl. J. Med. 358, 1160-1174.

Fung, C., Chen, X., Grandis, J. R., and Duvvuri, U. (2012). EGFR tyrosine kinase inhibition induces autophagy in cancer cells. Cancer Biol. Ther. 13.

Gazdar, A. F., and Minna, J. D. (1996). NCI series of cell lines: an historical perspective. J. Cell Biochem. Suppl. 24, 1-11.

Gorzalczany, Y., Gilad, Y., Amihai, D., Hammel, I., Sagi-Eisenberg, R., and Merimsky, O. (2011). Combining an EGFR directed tyrosine kinase inhibitor with autophagy-inducing drugs: a beneficial strategy to combat non-small cell lung cancer. Cancer Lett. 310, 207-215.

Han, W., Pan, H., Chen, Y., Sun, J., Wang, Y., Li, J., Ge, W., Feng, L., Lin, X., Wang, X., et al. (2011). EGFR tyrosine kinase inhibitors activate autophagy as a cytoprotective response in human lung cancer cells. PLoS One 6, e18691.

He, C., and Levine, B. (2010). The Beclin 1 interactome. Curr. Opin. Cell Biol. 22, 140-149.

Lemmon, M. A., and Schlessinger, J. (2010). Cell signaling by receptor tyrosine kinases. Cell 141, 1117-1134.

Levine, B., and Kroemer, G. (2008). Autophagy in the pathogenesis of disease. Cell 132, 27-42.

Lynch, T. J., Bell, D. W., Sordella, R., Gurubhagavatula, S., Okimoto, R. A., Brannigan, B. W., Harris, P. L., Haserlat, S. M., Supko, J. G., Haluska, F. G., et al. (2004). Activating mutations in the epidermal growth factor receptor underlying responsiveness of non-small-cell lung cancer to gefitinib. N. Engl. J. Med. 350, 2129-2139.

Matsunaga, K., Saitoh, T., Tabata, K., Omori, H., Satoh, T., Kurotori, N., Maejima, I., Shirahama-Noda, K., Ichimura, T., Isobe, T., et al. (2009). Two Beclin 1-binding proteins, Atg14L and Rubicon, reciprocally regulate autophagy at different stages. Nat. Cell. Biol. 11, 385-396.

Mizushima, N., Yoshimori, T., and Levine, B. (2010). Methods in mammalian autophagy research. Cell 140, 313-326.

Pao, W., and Chmielecki, J. (2010). Rational, biologically based treatment of EGFR-mutant non-small-cell lung cancer. Nat. Rev. Cancer 10, 760-774.

Rekhtman, N., Ang, D. C., Sima, C. S., Travis, W. D., and Moreira, A. L. (2011). Immunohistochemical algorithm for differentiation of lung adenocarcinoma and squamous cell carcinoma based on large series of whole-tissue sections with validation in small specimens. Mod. Path. 24, 1348-1359.

Rubinsztein, D. C., Codogno, P., and Levine, B. (2012). Autophagy modulation as a potential therapeutic target for diverse diseases. Nat. Rev. Drug Discov. 11, 709-730.

Saad, R. S., Liu, Y. L., Han, H., Landreneau, R. J., and Silverman, J. F. (2004). Prognostic significance of thyroid transcription factor-1 expression in both early-stage conventional adenocarcinoma and bronchioloalveolar carcinoma of the lung. Hum. Pathol. 35, 3-7.

Sato, T., Nakashima, A., Guo, L., Coffman, K., and Tamanoi, F. (2010). Single amino-acid changes that confer constitutive activation of mTOR are discovered in human cancer. Oncogene 29, 2746-2752.

Shim, H. S., Lee da, H., Park, E. J., and Kim, S. H. (2011). Histopathologic characteristics of lung adenocarcinomas with epidermal growth factor receptor mutations in the International Association for the Study of Lung Cancer/American Thoracic Society/European Respiratory Society lung adenocarcinoma classification. Arch. Pathol. Lab Med. 135, 1329-1334.

Tang, X., Kadara, H., Behrens, C., Liu, D. D., Xiao, Y., Rice, D., Gazdar, A. F., Fujimoto, J., Moran, C., Varella-Garcia, M., et al. (2011). Abnormalities of the TITF-1 lineage-specific oncogene in NSCLC: implications in lung cancer pathogenesis and prognosis. Clin. Cancer Res. 17, 2434-2443.

VanMeter, A. J., Rodriguez, A. S., Bowman, E. D., Jen, J., Harris, C. C., Deng, J., Calvert, V. S., Silvestri, A., Fredolini, C., Chandhoke, V., et al. (2008). Laser capture microdissection and protein microarray analysis of human non-small cell lung cancer: differential epidermal growth factor receptor (EGPR) phosphorylation events associated with mutated EGFR compared with wild type. Mol. Cell. Proteomics 7, 1902-1924.

Wang, R. C., Wei, Y., An, Z., Zou, Z., Xiao, G., Bhagat, G., White, M., Reichelt, J., and Levine, B. (2012). Akt-mediated regulation of autophagy and tumorigenesis through Beclin 1 phosphorylation. Science 338, 956-959.

Wang, Y., Pennock, S., Chen, X., and Wang, Z. (2002). Endosomal signaling of epidermal growth factor receptor stimulates signal transduction pathways leading to cell survival. Mol. Cell. Biol. 22, 7279-7290.

Yao, Y., Wang, G., Li, Z., Yan, B., Guo, Y., Jiang, X., and Xi, Z. (2010). Mitochondrially localized EGFR is independent of its endocytosis and associates with cell viability. Acta Biochim. Biophys. Sin. (Shanghai) 42, 763-770.

What is claimed is:

1. An antibody specific for Beclin 1 phosphorylated at Ser234, Ser295, Tyr229, Tyr233 or Tyr352.

2. The antibody of claim 1 wherein the antibody is specific for Beclin 1 phosphorylated at Ser 234.

3. The antibody of claim 1 wherein the antibody is specific for Beclin 1 phosphorylated at Ser 295.

4. The antibody of claim 1 wherein the antibody is specific for Beclin 1 phosphorylated at Tyr229.

5. The antibody of claim 1 wherein the antibody is specific for Beclin 1 phosphorylated at Tyr233.

6. The antibody of claim 1 wherein the antibody is specific for Beclin 1 phosphorylated at Tyr352.

7. A composition comprising the antibody of claim 1 specific for Beclin 1 phosphorylated at Ser234 and an Akt inhibitor different from the antibody.

8. A composition comprising the antibody of claim 1 specific for Beclin 1 phosphorylated at Ser295 and an Akt inhibitor different from the antibody.

9. A composition comprising the antibody of claim 1 specific for Beclin 1 phosphorylated at Tyr229 and an EGFR inhibitor different from the antibody.

10. A composition comprising the antibody of claim 1 specific for Beclin 1 phosphorylated at Tyr233 and an EGFR inhibitor different from the antibody.

11. A composition comprising the antibody of claim 1 specific for Beclin 1 phosphorylated at Tyr352 and an EGFR inhibitor different from the antibody.

12. A method of characterizing a Beclin 1 protein of a human cancer cell, comprising:
    detecting in the protein Ser234, Ser295, Tyr229, Tyr233 or Tyr352 phosphorylation with an antibody of claim 1.

13. A method of characterizing a Beclin 1 protein of a human cancer cell, comprising:
    detecting in the protein Ser234 phosphorylation with an antibody of claim 1.

14. A method of characterizing a Beclin 1 protein of a human cancer cell, comprising:
    detecting in the protein Ser295 phosphorylation with an antibody of claim 1.

15. A method of characterizing a Beclin 1 protein of a human cancer cell, comprising:
    detecting in the protein Ser234, Ser295, Tyr229, Tyr233 or Tyr352 phosphorylation with an antibody of claim 1, further comprising prescribing, initiating or continuing an Akt or EGFR inhibitor therapy for the person.

16. A method of characterizing a Beclin 1 protein of a human cancer cell, comprising:
    detecting in the protein Ser234, Ser295, Tyr229, Tyr233 or Tyr352 phosphorylation with an antibody of claim 1, wherein the detecting step comprises immunohistochemistry, immunostaining, immunofluorescence or western blot assay.

17. A method of characterizing a Beclin 1 protein of a human cancer cell, comprising:
    detecting in the protein Ser234, Ser295, Tyr229, Tyr233 or Tyr352 phosphorylation with an antibody of claim 1, wherein the cancer cell is of a tissue sample derived from the breast, pancreas, stomach, liver, secretory gland, bladder, lung, skin, prostate gland, ovary, cervix, uterus, brain, eye, connective tissue, bone, muscles or vasculature.

18. A method of characterizing a Beclin 1 protein of a human cancer cell, comprising:
    detecting in the protein Ser234, Ser295, Tyr229, Tyr233 or Tyr352 phosphorylation with an antibody of claim 1, wherein the cancer cell is of a tissue sample derived from a breast tumor, a lung carcinoma, a colon carcinoma, a cervical carcinoma, an adenocarcinoma, a melanoma, a leukemia, a lymphoma, a glioma, a neuroblastoma, a retinoblastoma or a sarcoma.

* * * * *

UNITED STATES PATENT AND TRADEMARK OFFICE
CERTIFICATE OF CORRECTION

Page 1 of 1

PATENT NO. : 9,671,412 B2
APPLICATION NO. : 14/667372
DATED : June 6, 2017
INVENTOR(S) : Beth C. Levine, Richard C. Wang and Yongjie Wei It is certified that error appears in the above-identified patent and that said Letters Patent is hereby corrected as shown below:

In the Specification

At Column 1, Lines 5-9, the acknowledgement of government funding should read:
--This invention was made with government support under Grant Numbers CA084254 and CA109618 awarded by the National Institutes of Health (NIH). The government has certain rights in the invention.--

Signed and Sealed this
Twenty-fifth Day of May, 2021

Drew Hirshfeld
*Performing the Functions and Duties of the*
*Under Secretary of Commerce for Intellectual Property and*
*Director of the United States Patent and Trademark Office*